(12) United States Patent
Gewiese

(10) Patent No.: US 7,723,986 B2
(45) Date of Patent: May 25, 2010

(54) INSTALLATION FOR INVESTIGATING OBJECTS USING MAGNETIC RESONANCE

(75) Inventor: Bernd Gewiese, Straubenhardt (DE)

(73) Assignee: Bruker Biospin MRI GmbH, Ettlingen (DE)

( * ) Notice: Subject to any disclaimer, the term of this patent is extended or adjusted under 35 U.S.C. 154(b) by 302 days.

(21) Appl. No.: 11/902,809

(22) Filed: Sep. 26, 2007

(65) Prior Publication Data

US 2008/0086023 A1 Apr. 10, 2008

(30) Foreign Application Priority Data

Oct. 5, 2006 (DE) ........................ 10 2006 047 589

(51) Int. Cl.
*G01V 3/00* (2006.01)
(52) U.S. Cl. ...................................... 324/307
(58) Field of Classification Search ......... 324/300–322; 600/407–445
See application file for complete search history.

(56) References Cited

U.S. PATENT DOCUMENTS

| 6,418,932 | B2 * | 7/2002 | Paschal et al. .............. 128/845 |
| 6,778,850 | B1 * | 8/2004 | Adler et al. ................. 600/427 |
| 6,817,143 | B2 * | 11/2004 | Porret et al. .................. 49/507 |
| 6,946,842 | B2 * | 9/2005 | Gozansky ................... 324/318 |
| 7,167,001 | B2 * | 1/2007 | Gewiese ..................... 324/318 |
| 7,597,104 | B2 * | 10/2009 | Zheng et al. ................ 128/869 |
| 2004/0251905 | A1 | 12/2004 | Gozansky |
| 2005/0200360 | A1 | 9/2005 | Gewiese |
| 2009/0076388 | A1 * | 3/2009 | Napoli et al. ............... 600/437 |
| 2009/0129545 | A1 * | 5/2009 | Adler et al. .................... 378/65 |
| 2009/0259121 | A1 * | 10/2009 | Simonetti et al. ........... 600/410 |
| 2009/0306494 | A1 * | 12/2009 | Scarth et al. ................ 600/411 |

FOREIGN PATENT DOCUMENTS

DE 196 39 975 5/1998

OTHER PUBLICATIONS

"Laboratory biosafety manual Third edition". World Health Organization Geneva 2004.

* cited by examiner

*Primary Examiner*—Brij B Shrivastav
(74) *Attorney, Agent, or Firm*—Paul Vincent

(57) ABSTRACT

An installation for investigating objects (10*a*) using magnetic resonance comprising a safety room (1) which has gastight walls (1*a-c*) and having a magnet system (9) for producing a homogenous magnetic field in an investigational volume (13), the magnet system (9) comprising a gastight outer shell (19) which is penetrated in a shell region (29) by feed-throughs (39*a-d*) into the interior of the magnet system (9), is characterized in that the magnet system (9) is arranged in the safety room (1), and one of the gastight walls (1*a-c*) is penetrated in an access region (1*e*), wherein a gastight connecting element (14) is present between the access region (1*e*) and the shell region (29) which, at its ends, is connected in a gastight manner to the gastight wall and the gastight outer shell (19) respectively, so that access from outside the safety room (1) is available to the shell region (29) and the feed-throughs there (39*a-d*), that access being sealed in a gastight manner with respect to the safety room (1). A part of the gastight shell of the magnet system thereby effectively becomes part of the wall of the safety room.

19 Claims, 3 Drawing Sheets

INSTALLATION FOR INVESTIGATING OBJECTS USING MAGNETIC RESONANCE

This application claims Paris Convention priority of DE 10 2006 047 589.5 filed Oct. 5, 2006 the complete disclosure of which is hereby incorporated by reference.

BACKGROUND OF THE INVENTION

The invention relates to an installation for investigating objects using magnetic resonance comprising a safety room which has gastight walls and a magnet system for producing a homogenous magnetic field in an investigational volume, the magnet system having a gastight outer shell which is penetrated in a shell region by feed-throughs into the interior of the magnet system.

An installation of this kind is known, for example, from the published patent application US 2005/200360 A1.

Research activities for the development of vaccines and therapies in conjunction with highly infectious viruses which can be transferred by aerosols, as well as research with gene manipulated and biologically, chemically or radioactively contaminated objects as well as poisonous chemical weapons (ABC weapons) all require a high level of safety precautions. Objects of this kind must, therefore, by investigated in a safety room from which no gas exchange is allowed to occur with the environment. The conditions for such safety rooms are, for example, described in the brochure "Laboratory Biosafety Manual", Third Edition 2004, of the WHO, in particular on pages 2 and 3. In many cases, the requirements of Biosafety Level 4 described therein have to be fulfilled. For research on the aforementioned objects, among other things, measurements using magnetic resonance are of interest. Since devices arranged within the safety room can also become contaminated, these devices can no longer be used to investigate non-contaminated objects. Therefore, separate devices are generally required for the investigation of contaminated and non-contaminated objects. The acquisition of a plurality of devices for measuring magnetic resonance is, however, associated with considerable cost.

The maintenance of devices arranged in contaminated spaces represents an additional problem, since maintenance personnel have to spend time in the safety room during the maintenance procedure, for example when filling liquid helium for the superconducting coils of the device. This requires additional safety measures to protect the personnel (protective suits, disposal of the protective clothing, health monitoring of the personnel and the like) and involves considerable risks for the technical personnel, in particular since the risks associated with contamination are often underestimated on the part of the technical personnel. A large portion of the maintenance work is, therefore, generally carried out by scientifically trained personnel, whereby the maintenance costs are unnecessarily increased.

In particular, for example, for the investigation of gene manipulated animals extremely high safety precautions are required to prevent the escape of the animals. The animals are generally investigated in an anaesthetized condition. Should the animal regain consciousness prematurely, these gene manipulated animals have to be prevented from escaping.

In the aforementioned published patent application, the stated problems are solved by the magnet being located outside the safety room, but the investigational volume being located on the inside. This is achieved by a safety room comprising an extension which projects into the magnet system and encloses the investigational volume.

Such an extension is, however, topologically complicated and difficult to produce, since it has to remain sealed even in the event of accidents. Additionally, the design of the installation considerably deviates from previous MRI investigating rooms with integral radio frequency (=RF) shielding, which further increases the complexity and costs.

By far, the most frequent maintenance tasks by non-scientific personnel take place on the magnet system and it appears to be completely acceptable to design the installation such that it is only during such work that the safety room must not be entered.

It is therefore the object of the invention to propose an installation for investigating contaminated objects using magnetic resonance, in which simple maintenance of the magnet system is possible without risk of contamination for the maintenance personnel, which is as simple and robust as possible and which deviates little from standard investigating rooms.

SUMMARY OF THE INVENTION

This object is achieved in a surprisingly simple, but effective, manner by an installation with the features described above, in which the magnet system is arranged in the safety room, one of the gastight walls being penetrated in an access region and a gastight connecting element being present between the access region and the shell region which, at its ends, is connected in a gastight manner to the gastight wall and the gastight outer shell respectively, so that access from outside the safety room is available to the shell region and the feed-throughs there, the access being sealed in a gastight manner with respect to the safety room.

Thus one part of the gastight shell of the magnet system is effective for one part of the wall of the safety room, whilst the shell region enclosed by the connecting element is accessible for maintenance purposes.

The safety room or at least a measuring room inside the safety room is advantageously configured as an RF-tight Faraday cage. The connecting element and the part of the outer shell which does not form part of the enclosed shell region, thus also form part of the Faraday cage which seals the safety room and/or the measuring room with regard to RF.

The installation according to the invention allows a topological separation of the maintenance region of the magnet arrangement from the safety room. The technical support and maintenance of the magnet system may, therefore, be carried out by technical staff, without the technical staff having to enter the safety area. Unnecessary danger to the technical personnel is avoided by the installation according to the invention. Additionally, the installation generates improved safety of the objects to be investigated relative to the environment, as the risk of the escape of contamination and/or of the object itself is reduced, since the safety room must not be entered for these purposes. Moreover, the arrangement is topologically more simple than the installation described above, which makes the installation more robust and more secure against a tendency to leaks.

The advantages of the invention are particularly effective in one embodiment in which the object to be investigated is contaminated and the safety room is configured such that no contamination is able to penetrate to the outside from the safety room, in particular when the requirements of the aforementioned Biosafety Level 4 have to be fulfilled.

Preferably, low pressure prevails in the safety room relative to the external atmosphere. This guarantees that, in the event of a possible occurrence of a leakage in the installation, there is gas transfer from the outside into the safety room and not vice versa.

It is advantageous if the safety room is accessible through at least one lock. Due to the generally small volume of the lock, poisonous gases or aerosols can be pumped off from the lock room relatively quickly. This is particularly advantageous for exchanging and disposing of contaminated protective clothing.

In a particularly preferred embodiment of the invention, the safety room is provided with an air filtering system $1d$ or is connected to such a system. Air which is infected with poisonous substances and/or with viruses can be pumped out of the room through the air filtering system $1d$ and can be filtered and cleaned. With the assistance of a controlled air exchange, entry into the safety room, for example to remove objects, is made significantly easier.

In an advantageous embodiment of the invention, the object to be investigated is arranged during the investigation in a closed container. Small objects, in particular, can be easily handled in this manner. The escape from the laboratory of, for example, an animal to be investigated is thereby rendered more difficult.

Moreover, it may be advantageous when single-use RF-antennae are provided in the safety room which are disposed of after use, so that a transmission of the contamination via an RF-antenna, which has already been used, to a different object is avoided.

A control room and/or maintenance room, in which a console and/or a power supply unit are located, is preferably disposed adjacent to the safety room. The inside of the safety room may be viewed through a gastight and RF-tight window. This has the advantage that the operator of the installation does not personally have to enter the safety room and nevertheless has the magnet system with the investigating volumes in sight.

A filter plate, which is gastight and RF-tight, is also advantageously located in the wall between the two rooms, and through which the ducts lead to and from the magnet system. Not all ducts have to run via the connecting element, which is topologically expensive. Fixedly installed, low maintenance connections may also be directly passed through the filter plate.

The penetrated wall is preferably the ceiling of the safety room. The feed-throughs into the magnet system are generally connected at the top or may be displaced therein. With a superconducting magnet system the feed-throughs are substantially the tower(s) of the cryostat with the apertures for the supply and removal of the liquefied gases as well as for electrical feed-throughs, in particular, for charging and discharging the magnetic coils or a cold head of a refrigerator.

The connecting element preferably consists of metal, in particular stainless steel. Metal surfaces may be particularly easily decontaminated. Additionally, a metal wall undertakes the further function of the RF-shielding of the investigating room.

The connecting element is preferably welded to the penetrated wall and/or to the gastight outer shell. A welded connection may be mechanically loaded, is reliably gastight and also RF-tight.

It is particularly preferred when the connecting element consists of a first partial connecting element which is fixedly connected to the penetrated wall as well as of a second partial connecting element which is fixedly connected to the gastight outer shell, and in that the two partial connecting elements are in turn connected in a gastight manner. This facilitates the installation and (temporary) dismantling of the installation.

The connection of the connecting element to the wall and/or the gastight shell and/or the connection of the partial connecting elements to one another are preferably welded connections, which ensures mechanical rigidity and tightness.

An embodiment is advantageous in which the connecting element is funnel-shaped with a larger opening on the wall side, such that there is easier access to the feed-throughs from outside the safety room.

The invention is particularly advantageous if the magnet system comprises a superconducting magnetic coil, and the gastight shell is the outer periphery of a magnet cryostat. In this case, the feed-throughs are particularly advantageously positioned.

Preferably, therefore, the feed-throughs comprise such feed-throughs for power leads for the magnetic coils and/or for shim coils and/or filling ducts and evaporating ducts and/or quench ducts for cryogenic fluids present in the cryostat, in particular helium. These are the most maintenance-intensive components of the magnet system. In particular the quench duct must be securely guided to the outside, in order not to lead to overpressure in the safety room during a quench, which could negatively interfere with the function thereof.

The cold head of an optional cryostat refrigerator is advantageously arranged in the shell region. It may thus be supplied, maintained and/or replaced through the connecting element from outside the safety room.

The connecting element or one or both of the partial connecting elements may contain flexible portions, preferably in the form of a (metallic) bellows. The position of the magnet system relative to the wall may therefore be easily altered for installing and/or adjusting. In particular during installation, it is possible to compensate easily for small tolerances.

In the event of an accident caused, for example, by a quench of a superconducting magnet in which the helium tank ruptures and an overpressure is produced in the vacuum part, overpressure inside the magnet system wall spreads as far as the outer shell. A large-surface overpressure valve is therefore generally provided on the outer shell. It is therefore advantageous to provide said overpressure valve with an overpressure duct, which leads out of the safety room through a gastight feed-through, through the connecting element. As a result, in this extreme case of an accident, helium does not enter the safety room and endanger personnel there or lead to overpressure.

Further advantages of the invention are given in the description and the drawings. The aforementioned features and the features to be still further described may also be applied per se or to a plurality of elements in any combination. The embodiments shown and described are not understood to be a definitive list but have characteristics given by way of example for explaining the invention.

DESCRIPTION OF THE PREFERRED EMBODIMENT

Figure 1:
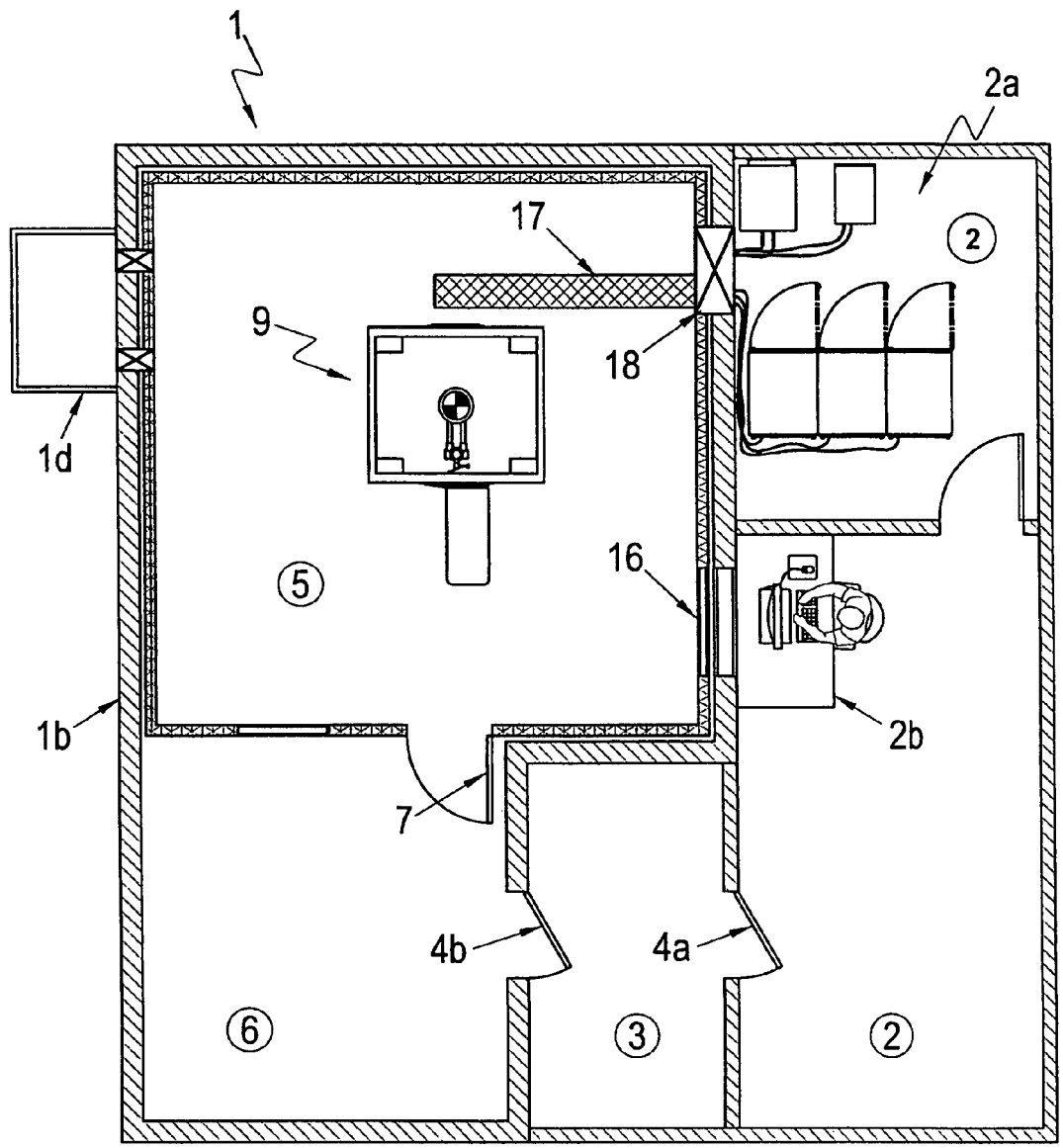
FIG. 1 schematically shows an installation according to the invention for investigating objects by means of magnetic resonance in a safety room with an integrated Faraday cage and superconducting magnet system in plan view.
Figure 2:
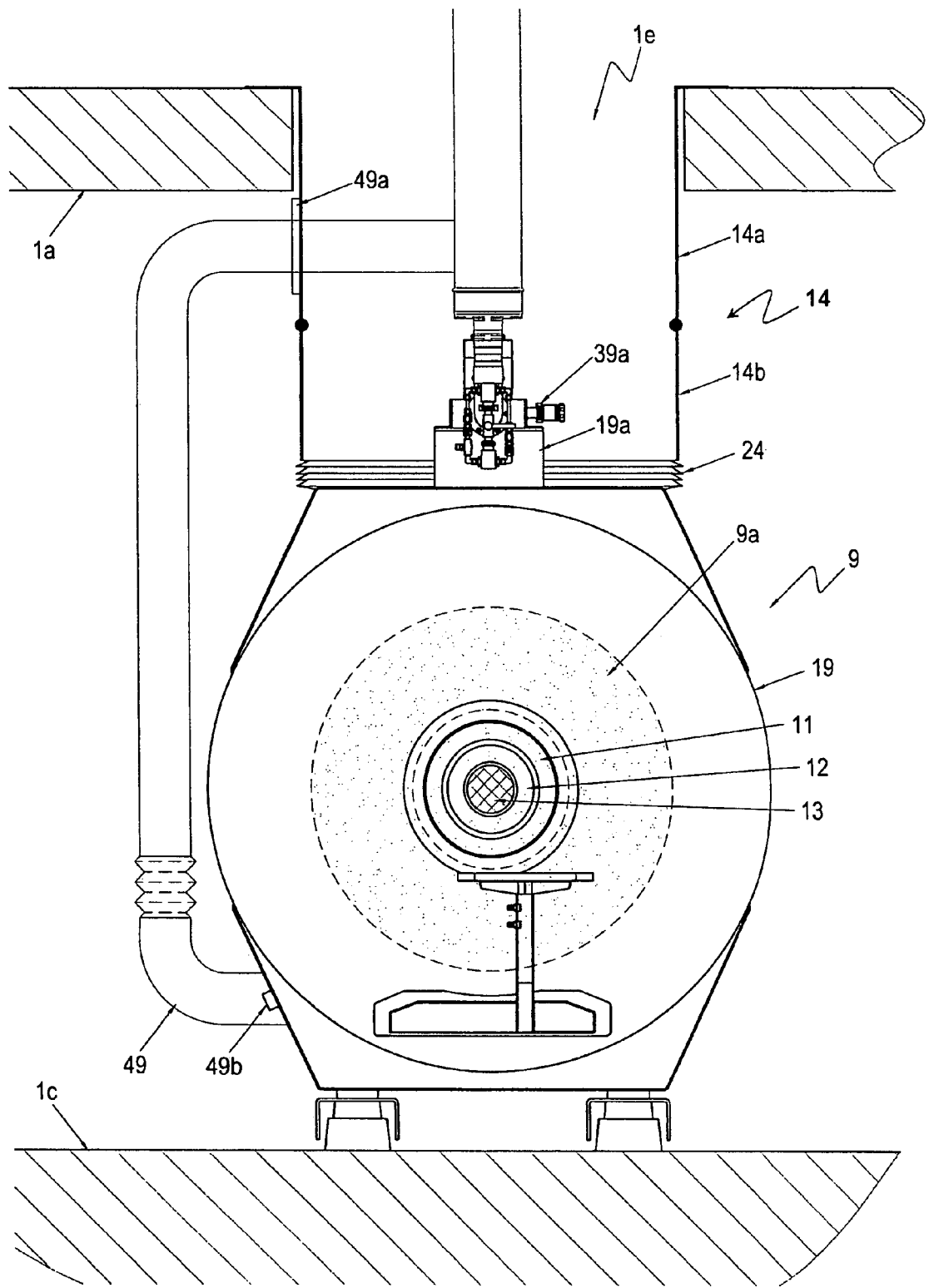
FIG. 2 schematically shows a detail of the installation of FIG. 1 in a side view transversely to the horizontal longitudinal axis of the superconducting magnet system.
Figure 3:
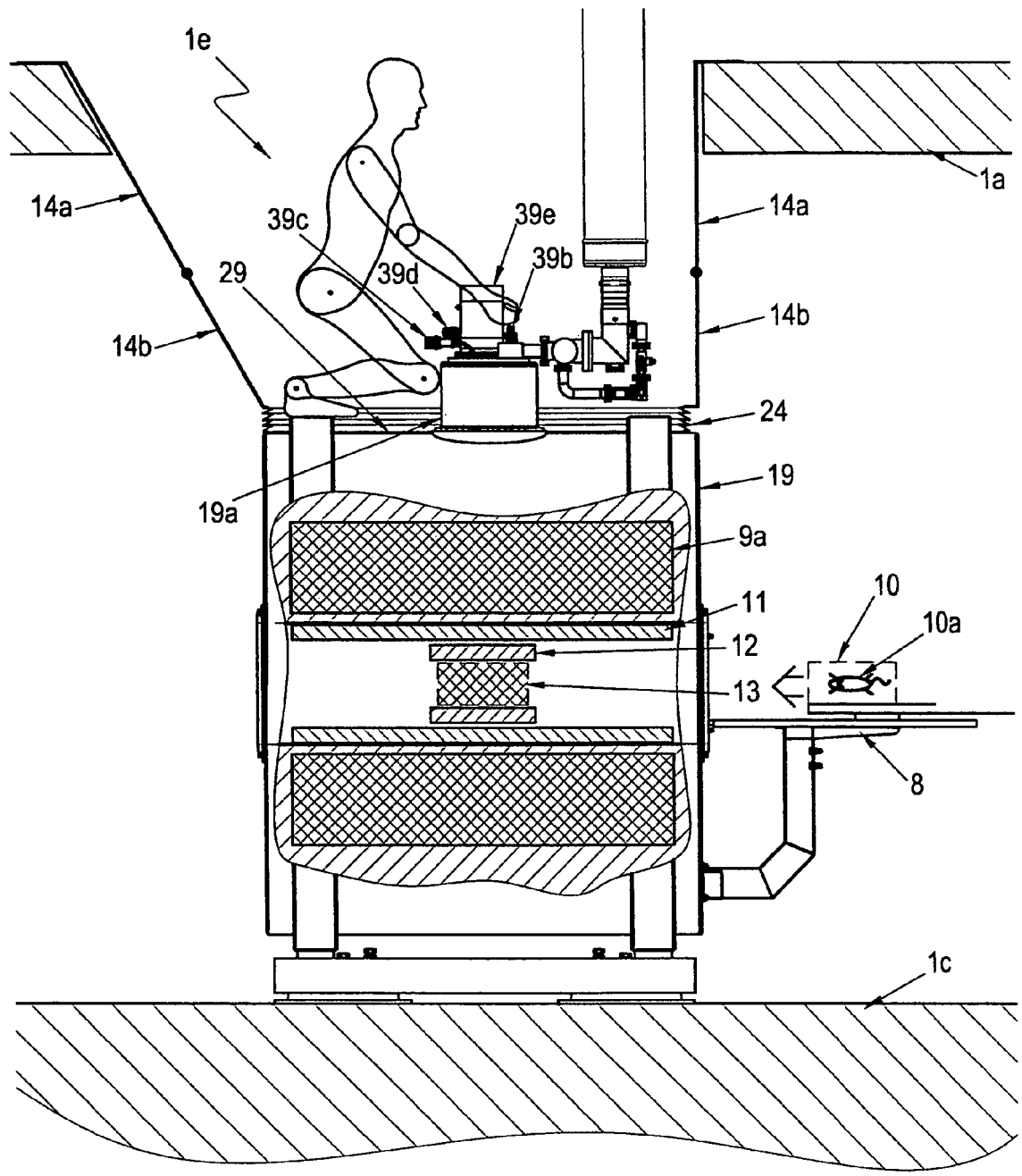
FIG. 3 shows schematically a detail of the installation of FIG. 1 in a side view along the horizontal longitudinal axis of the superconducting magnet system.

FIGS. 1 to 3 are discussed together and show an embodiment of an installation for investigating objects using magnetic resonance, which comprises a safety room 1. The safety room 1 may be entered from a control room and maintenance room 2 via the doors 4a and 4b which are closed in a gastight and pressure-proof manner through a lock 3. The safety room 1 is divided up into a measuring room 5 and an object preparation room 6, which are also separated from each other by means of an RF-tight door 7. The measuring room is configured as a Faraday cage (including the connecting element 14 to be discussed further and the outer shell 19 of the magnet system 9). All measuring and anaesthetic devices necessary for experiments are located in the safety room 1. The measuring object 10a can be prepared for the measurement using a transportable object pallet 8.

A superconducting magnet system 9 is arranged in the measuring room 5 which also comprises shim coils and gradient coils 11 and one or more resonators 12. The investigational volume 13 in which the measurements are carried out using magnetic resonance, is located within the resonator 12 and is accordingly surrounded by the magnet system 9.

The walls of the safety room 1, i.e. the ceiling 1a, side walls 1b and floor 1c are gastight and substantially consist of metal. The ceiling 1a is penetrated in an access region 1e above the magnet system 9. A funnel-shaped connecting element 14 made of stainless steel connects the penetrated ceiling 1a to the stainless steel outer shell 19 of the magnet system 9. The connecting element 14 consists of two parts 14a, 14b which in the assembled state are welded together in a gastight manner. The first part 14a is welded to the ceiling 1a in a gastight manner. The second part 14b is welded in a gastight manner to the gastight outer shell 19 of the magnet system 9 and comprises a bellows 24 made of stainless steel, such that a shell region 29 of the outer shell 19 is effectively located outside the safety room 1 and is separated therefrom by the welded connecting element 14 in a gastight manner and is accessible from outside via the access region 1e. In this shell region 29 are preferably located on the towers 19a of the cryostat, feed-throughs 39a-39d into the interior of the magnet system 9, in this case of a cryostat with a horizontal bore, which contains a superconducting magnetic coil. Furthermore, in this shell region 29 the cold head 39e of a refrigerator is located which cools radiation shields and/or evaporating helium in the interior and to which electrical and gas lines lead. The general construction of such a magnet system 9 forms part of the prior art and does not need to be explained further. The feed-throughs 39a-39d and the cold head 39e of the refrigerator are, during normal operation of the installation, substantially closed (apart from an evaporation duct for evaporating helium). They may, however, be opened without entering the safety room 1 for maintenance purposes, for example to introduce current-carrying rods for charging (discharging) the coils, for inserting a siphon for refilling with helium, to open the cold head housing for cleaning purposes or to replace parts. The gas lines to the cold head 39e form, during normal operation, a closed system including an external compressor. In the event of a quench of the magnetic coil 9a in the cryostat 9 an evaporating duct of large cross-section has to be opened, the so-called quench duct. All these supply and discharge ducts lead from outside through the connecting element 14 to the feed-throughs 39a-d in the shell region 29 and/or back again. Additionally, the shell region 29 has to be accessible from outside for maintenance purposes. For this reason, the connecting element 14 has an overall funnel shape. The division into two partial regions 14a, 14b which respectively are fixedly connected to the room ceiling 1a and/or the cryostat shell 19, allows a relatively simple assembly and/or disassembly after decontamination of the safety area 1 with a separation into a relatively uncritical and accessible point. After separation, the partial elements 14a, 14b may remain on the ceiling 1a and/or on the cryostat 9, when it is intended to subsequently connect these again. The bellows 24 allows a simple connection before welding and additionally acts in a vibration damping manner.

By means of the transportable object pallet 8, a prepared object 10a may be transferred into the investigational volume 13. The measuring console 2b of the device and possible power supply units 2a are preferably accommodated in a further room 2, which is not subject to the safety requirements of the safety room 1 and thus is fully accessible. Ducts 17 lead from the console 2b and/or the power supply unit 2a through a gastight and RF-tight filter plate 18 in the wall to the magnet system. These ducts 17 may comprise the RF supply lines to the resonators 12, power leads to the shim system and gradient system 11 or also ducts for supplying the measuring object 10 as well as coolant ducts for the gradient system 11.

During measurement of magnetic resonance, radio frequency pulses are transmitted from and received by an RF antenna (resonator) 12. For some investigations it is necessary to move the RF receiving antenna 12 very close to, or even in contact with, the object 10a to be investigated. For such applications, the invention therefore provides RF measuring antennae and/or RF transmitting antennae 12 in the safety room which are single-use coils, and which can be disposed of after the investigation of the object 10a in order to avoid contamination of the object to be subsequently investigated by the contaminated RF receiving antennae 12. The measuring signals received by the RF measuring antenna and/or RF receiving antenna 12 are then transmitted from the safety room 1 to the console 2b by means of electrical lines 17 which are passed through the gastight filter plate 18 or even by means of wireless, in particular optical, signal transmission means.

An overpressure valve 49b of the vacuum part of the cryostat 9 is located in the lower region of the outer shell 19 of the magnet system. This overpressure valve 49b is connected via an overpressure duct 49 to a feed-through 49a through the connecting element 14, so that in the event of an accident, gas escaping at overpressure from the magnet system does not reach the safety room 1.

The installation according to the invention is not restricted for use in connection with magnetic resonance imaging measurements (MRI) but is also important for carrying out, for example, ESR spectroscopy or NMR spectroscopy, in particular for investigating ABC weapons. To this end, for example, it is conceivable to use a magnet system with a vertical bore.

As a whole, an arrangement is produced for measuring magnetic resonance by means of which highly contaminated objects, which are associated with a particular risk for human health and/or the environment, may be investigated, the installation according to the invention permitting simple and low-risk maintenance of the magnet system. The maintenance personnel are, therefore, not subject to unnecessary danger so that maintenance on the device can be carried out by technical personnel.

I claim:

1. An installation for investigating an object using magnetic resonance, the installation comprising:
   a gastight wall structure defining a safety room;
   a magnet system for producing a homogenous magnetic field in an investigational volume;
   a gastight outer shell disposed about said magnet system, said gastight outer shell having a shell region structured and dimensioned to facilitate access into an interior of said magnet system;
   a gastight connecting element defining an access region, said gastight connecting element connected in a gastight manner between said gastight wall structure and said gastight outer shell, proximate said shell region; and
   feed-throughs passing between said gastight connecting element and said shell region, wherein said gastight connecting element provides access to said feed-throughs and said shell region from outside said safety room, said access being sealed in a gastight manner with respect to said safety room, wherein said connecting element comprises a first partial connecting element which is fixedly connected to said wall structure and a second partial connecting element which is fixedly connected to said gastight outer shell, wherein said first and said second partial connecting elements are, in turn, connected to each other in a gas tight manner.

2. The installation of claim 1, wherein the object to be investigated is contaminated, said room being configured such that no contamination can penetrate to an outside of said safety room or such that the specifications of "Biosafety Level 4" are observed.

3. The installation of claim 1, wherein low pressure prevails in said safety room relative to an external atmosphere.

4. The installation of claim 1, wherein said safety room is accessible through at least one lock.

5. The installation of claim 1, wherein said safety room has an air filtering system or is connected to such a system.

6. The installation of claim 1, wherein the object to be investigated is disposed in a closed container during investigation.

7. The installation of claim 1, wherein single-use RF antennae are provided in said safety room, said antennae being structured for disposed thereof after use.

8. The installation of claim 1, further comprising a control or maintenance room disposed adjacent to said safety room, said control or maintenance room having a console and/or a power supply unit, wherein a wall between said safety room and said control or maintenance room comprises a gastight and RF-tight window.

9. The installation of claim 8, wherein a wall disposed between said safety room and said control or maintenance room comprises a filter plate having ducts.

10. The installation of claim 1, wherein said gastight connecting element is disposed at a ceiling of said safety room.

11. The installation of claim 1, wherein said connecting element comprises metal or stainless steel.

12. The installation of claim 1, wherein said connecting element is welded to at least one of said wall structure and said outer shell.

13. The installation of claim 1, wherein said first and said second partial connecting elements are welded to each other.

14. The installation of claim 13, wherein said connecting element comprises flexible portions or metallic bellows.

15. An installation for investigating an object using magnetic resonance, the installation comprising:
   a gastight wall structure defining a safety room;
   a magnet system for producing a homogenous magnetic field in an investigational volume;
   a gastight outer shell disposed about said magnet system, said gastight outer shell having a shell region structured and dimensioned to facilitate access into an interior of said magnet system;
   a gastight connecting element defining an access region, said gastight connecting element connected in a gastight manner between said gastight wall structure and said gaslight outer shell, proximate said shell region; and
   feed-throughs passing between said gastight connecting element and said shell region, wherein said gastight connecting element provides access to said feed-throughs and said shell region from outside said safety room, said access being sealed in a gastight manner with respect to said safety room,
   wherein said connecting element is funnel-shaped with a larger opening on a wall structure side thereof to facilitate access to said feed-throughs from outside said safety room.

16. An installation for investigating an object using magnetic resonance, the installation comprising:
   a gastight wall structure defining a safety room;
   a magnet system for producing a homogenous magnetic field in an investigational volume;
   a gastight outer shell disposed about said magnet system, said gastight outer shell having a shell region structured and dimensioned to facilitate access into an interior of said magnet system;
   a gastight connecting element defining an access region, said gastight connecting element connected In a gastight manner between said gastight wall structure and said gastight outer shell, proximate said shell region; and
   feed-throughs passing between said gastight connecting element and said shell region, wherein said gastight connecting element provides access to said feed-throughs and said shell region from outside said safety room, said access being sealed in a gastight manner with respect to said safety room,
   wherein said magnet system comprises a superconducting magnetic coil and said gastight outer shell is an outer periphery of a magnet cryostat.

17. The installation of claim 16, wherein said feed-throughs comprise power leads to magnetic coils and/or shim coils, filling ducts, evaporation ducts, and/or quench ducts for cryogenic fluids or helium present in said cryostat.

18. The installation of claim 16, further comprising a refrigerator cold head disposed in said shell region to which access is provided from outside said safety room via said connecting element.

19. The installation of claim 16, further comprising an overpressure valve disposed on said gastight outer shell outside said shell region, and a gastight overpressure duct connected between said overpressure valve and said connecting element.

* * * * *